July 5, 1955 J. D. BROWNELL Plant Pat. 1,405
ROSE PLANT
Filed Oct. 8, 1954
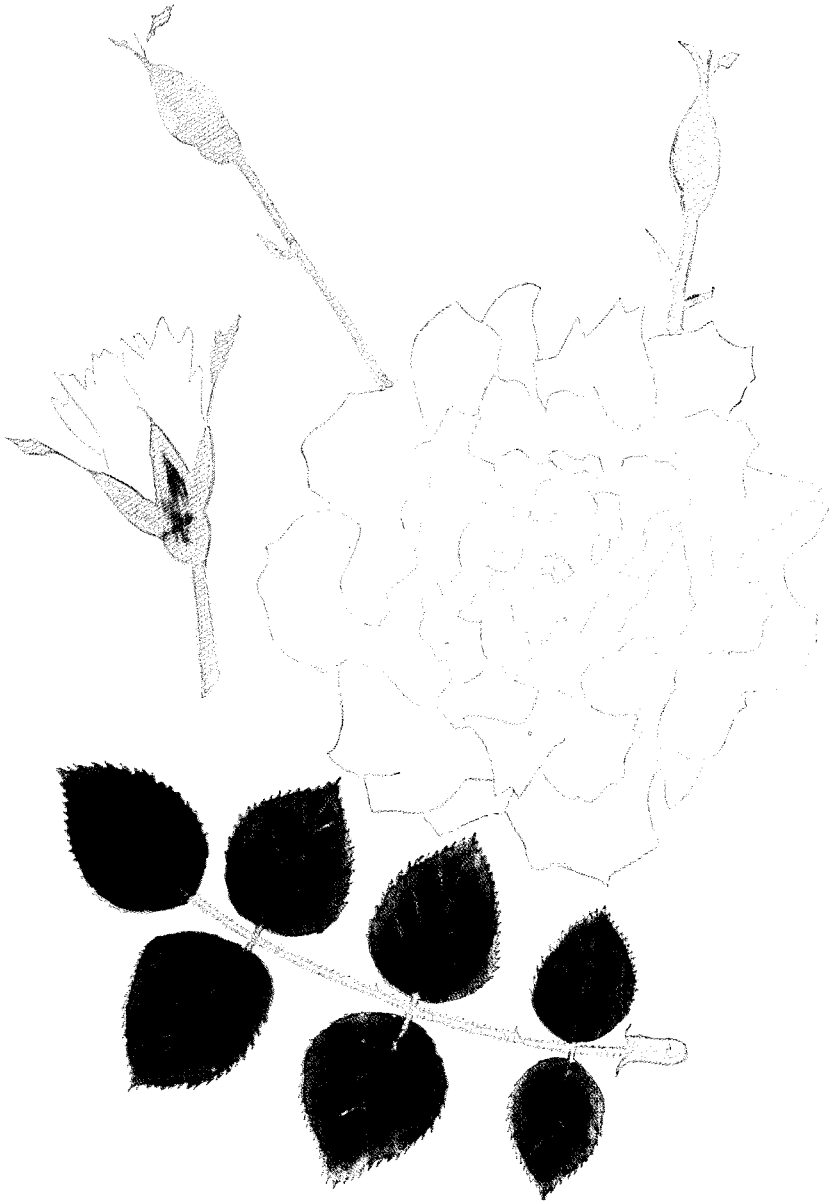
INVENTOR.
Josephine D. Brownell.

United States Patent Office

Plant Pat. 1,405

Patented July 5, 1955

1,405

ROSE PLANT

Josephine D. Brownell, Little Compton, R. I.

Application October 8, 1954, Serial No. 461,299

1 Claim. (Cl. 47—61)

My invention or discovery relates to roses and especially to a new, original and distinct variety of rose plant of the class known commercially as "hybrid teas" and is a variant in that class, being a *Rosa wichuraiana* hybrid tea hybrid, discovered by me and under my direction in the breeding grounds of my research gardens in Little Compton, Rhode Island, which can be and has been asexually reproduced.

My new rose plant is new as to the following characteristics and especially as to their joint association with the characteristics inherited from *Rosa wichuraiana,* of hardiness, or immunity from serious injury on account of cold temperatures prevailing in certain parts of the northern United States;

The yellow color (ordinary dictionary definition) of its petals, in combination with the unique brilliance thereof and their tendency to hold these colors under exposure, and the informal arrangement to the petals.

The notable resistance to blackspot;

The novelty and variation with certain definite limits of the form of the bloom, its character of holding that form for a long time and the petallage of the flowers;

Its character of fragrance;

Its unusual abundance of flowers, at bloom time and after early bloom time and until frost;

The intensity of its remontant and everblooming or reblooming character.

Its character of ascending in height by recurrent branching and progressively longer stems from the base in some instances long enough to be classified as canes;

The character of producing many seven leafleted leaves, which character seldom has obtained on hybrid teas not having *Rosa wichuraiana* ancestry, but frequently obtains on flower stems of descendants of *Rosa wichuraiana* of the dwarf reblooming type;

And especially its characteristic of freedom from premature defoliation by blackspot, under certain definite conditions of exposure, without any cultural control.

The color of my new rose is yellow.

ESSENTIAL INFORMATION

*Type*

Hybrid tea, *Rosa wichuraiana* hybrid, dwarf for garden display, cut flower and forcing or growing under glass.

*Class*

Hybrid tea crossed with *Rosa wichuraiana,* further restricted by originator to include only those varieties that can survive moderately low sub-zero temperatures.

*Breeding*

It came into being as a sport of the variety "Orange Ruffels," Plant Patent No. 1,124, discovered by me and by my assistants and co-worker, on the 10th day of July 1951[1], growing in my field at Little Compton, Rhode Island.

I have since made and directed extensive propagations and tests of this variety and flower.

Plants of this variety budded from the stem on which this sport obtained on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August in 1952 and 1953, inclusive and the characters have successively reproduced, true to the original sport.

FLOWER

*Habit*

It blooms out of doors in Little Compton, beginning about three days prior to the average beginning time of commercial hybrid teas and continues relative to growth of the plant until frost.

*Flowers borne*

Often one and frequently two or three or more on each stem, in the usual hybrid tea type of cluster. The pedicels and peduncles are medium small in diameter and medium in length, erect, stiff, smooth, free from prickles and bristles. Stems are long, diameter medium and notably stiff and rigid.

*Quantity of bloom*

Free, being cumulative in quantity from year to year as the plant increases in size, flowering through the summer.

*Fragrance*

Distinctive, pleasing China tea in combination with that of *Rosa wichuraiana,* under favorable environment.

*Bud*

Neck normal as described, opens well, being little to not at all affected by hot or wet weather or both, as to color and form, except at very high temperatures the color is less intense and the form of the petals is less recurled.

Before the calyx breaks the size is medium, form moderately pointed, frequently with one or more sepals having foliaceous parts extending beyond the apex of the calyx up to about one half of an inch, the number and size of the foliaceous parts being variable, otherwise the sepals are usually normal and regular, tapering to lanceolate at their apex, turning back nearly perpendicular to the pedicel as the bud opens.

Color of bud as calyx opens, outside at base Sulphur Yellow at 1/1 shading upward to Straw Yellow at 604/1; color reference to English Horticultural Color Chart.[2]

*Bloom*

As the bud opens and the flower develops to maturity the colors start as above and slowly soften, maintaining for an unusually long time the yellow shades above described, and as bud opens to maturity several outer rows variable in number, petals both sides same; inner rows of petals progressively toward center. All petals slowly softening both sides to Chinese Yellow at 605/3; both sides Chinese Yellow at 601/1.

The flower usually varies in size from four to five inches in diameter when fully open, petals average between 35 and 50, frequently some smaller petals and petaloids in the center, variable in number.

The flower opens high centered, informal, recurled, side curled, warped with terminal edge often waved and

[1] This and other dates herein are approximate.
[2] Color references to same unless otherwise indicated.

crinkled closely resembling ruffles with late display of stamens and pistils. The petals are variable from obovate to ovate to irregular and frequently with surfaces of the smaller petals frequently notably irregular. Texture is medium to thick both sides brilliant with slight veining which is not prominent. The time of opening in favorable conditions is four to six days.

The petals are substantial and after about five to six days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

*Reproductive organs*

Stamens, quantity variable, of slightly uneven length.

Anthers, Burnt Orange o14/3. Filaments, nearly Maize Yellow at 607/1.

Pistils are several of slightly uneven lengths, averaging around one-half inch long.

Ovaries are usually all inclosed.

Hips frequently develop to ovoid to globular, color comparable with that of leaves with variable colored overlay on the side exposed to the sun, moderately smooth; walls, thin, fleshy, medium in size.

Sepals are persistant and break off easily.

PLANT

*Foliage*

Is abundant, of compound leaves of three to five leaflets near the flower, five leaflets lower down the stem and frequently seven leaflets in the middle of the stem and nearer the base. Size of leaflets medium, averaging in size about half way between the average hybrid tea and the *Rosa wichuraiana* leaflets. As the plants develop in size some of the leaflets develop to one half larger than the size described above. Form of leaflets usually ovate with apex moderately acute, base rounded frequently slightly acute, margins with pointed serrations, petiolules short.

The leaflets average in width about two-thirds of their length.

Color references hereinafter are to Robert Ridgway Color Standard.

Color of leaflets on the upper surface is slightly variable from Dark Dull Yellow Green, with reverse side nearly Asphodel Green.

The rachises are medium, moderately narrow to slender, upper side smooth except some very short hairs on edges. Under side moderately smooth, usually 3 to 5 short prickles.

Stipules are medium, averaging about one-half of an inch long, with sharp points proportionally longer than usual, the upper edges of which normally form an angle of about 60 degrees.

Habit, dwarf; upright, compact, due to constitutional factors inherited from *Rosa wichuraiana;* more cumulative in growth from year to year than the normal hybrid tea rose plant, by stems from the base and by rebranching and growth and enlargement and extension of the stems from the base. The growth is moderately free at first, developing more rapidly after one or two years.

A notable difference from most rose plants is in the manner of growth of the stems. The leaves being closer together on the stems more eyes than normal are produced and more stems grow therefrom, thus increasing the production of blooms.

Color of mature stems is the same as that of the upper surface of mature leaves, shading variously lighter.

Prickles, several, frequently two to four between leaves, averaging in length about one-quarter inch, shading from the color of the stems to lighter, turning lighter throughout and later to nearly colorless. The entire plant is notably free from hairs.

*Disease resistance*

As a more exact description of the degree of blackspot resistance of my new rose I use the word nonsusceptible, defined as follows: The leaflets exposed to spores of blackspot will not become for them a culture medium (will not become infected) provided the leaflets are in normal healthy growing condition; however if damaged by frost or injury or otherwise deprived of normal vegetative opportunity such leaflets may take blackspot but cannot transmit it to healthy growing leaflets.

*Winter resistance*

A notable characteristic of this new rose is the resistance to moderate sub-zero temperatures in combination with its hybrid tea character and its *Rosa wichuraiana* ancestry. This variety with grafted bud and plant above that bud entirely exposed above ground to moderate sub-zero temperatures survived and bloomed normally the following season. The word temperature refers to the Fahrenheit scale.

*Comparisons*

My new rose is a sport from the sport parent "Orange Ruffels," Plant Patent No. 1,124. Both varieties are technically nonsusceptible to blackspot, being immuned thereto in a very definite degree to a great extent.

I know of no other yellow rose that is immuned to this extent.

They are both hybrids of *Rosa wichuraiana.*

The rose, known to me, that most nearly resembles my new rose is the variety "V for Victory," Plant Patent No. 543, the latter being a larger and more formal in its petal arrangement. The fragrance is different and the size of the leaflets is larger, and the form of growth of the plant is more open and less compact.

I claim:

A new and distinct variety of rose plant substantially as shown and described, characterized by its unique color, form, arrangement, bloom cluster, habit of growth and resistance to moderate sub-zero temperatures and to blackspot.

No references cited.